United States Patent
Henning

(10) Patent No.: US 7,516,847 B2
(45) Date of Patent: Apr. 14, 2009

(54) BIOCIDAL BLOOD GLUCOSE STRIP AND LANCET OR SHARPS DISPOSAL DEVICE

(75) Inventor: Sienna Lea Henning, Fishers, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 716 days.

(21) Appl. No.: 11/151,971

(22) Filed: Jun. 14, 2005

(65) Prior Publication Data

US 2006/0278545 A1    Dec. 14, 2006

(51) Int. Cl.
  B65D 83/10    (2006.01)
  B65D 69/00    (2006.01)

(52) U.S. Cl. .................. 206/569; 206/366; 206/572

(58) Field of Classification Search ......... 206/363–370, 206/223, 234, 569–572; 220/908; 422/58
See application file for complete search history.

(56) References Cited

U.S. PATENT DOCUMENTS

| | | | |
|---|---|---|---|
| 4,488,643 A | 12/1984 | Pepper et al. | |
| 4,702,385 A * | 10/1987 | Shillington et al. | 220/908 |
| 4,723,950 A | 2/1988 | Lee | |
| 4,816,307 A | 3/1989 | Honeycutt | |
| 4,880,602 A | 11/1989 | Al-Sioufi | |
| 4,971,261 A | 11/1990 | Solomons | |
| 5,003,892 A | 4/1991 | Bricken | |
| 5,104,390 A | 4/1992 | Yum et al. | |
| 5,167,193 A * | 12/1992 | Withers et al. | 206/366 |
| 5,245,117 A * | 9/1993 | Withers et al. | 206/366 |
| 5,354,132 A | 10/1994 | Young et al. | |
| 5,363,862 A | 11/1994 | Mercier | |
| 5,411,193 A | 5/1995 | Culp | |
| 5,447,237 A | 9/1995 | Carter et al. | |
| 5,674,175 A | 10/1997 | Bailey | |

(Continued)

FOREIGN PATENT DOCUMENTS

EP    0 633 004 A1    1/1995

(Continued)

OTHER PUBLICATIONS

International Patent Application PCT/EP2006/005610 Extended Search Report mailed Aug. 3, 2006.

*Primary Examiner*—Luan K Bui
(74) *Attorney, Agent, or Firm*—Woodard, Emhardt, Moriarty, McNett & Henry LLP

(57) ABSTRACT

A disposal receptacle having a biocidal interior surface for storing contaminated biotesting devices therein. The receptacle contains a one-way opening or valve to prevent used biotesting devices and bodily fluid from escaping or being removed from the receptacle; however, the one-way opening allows for insertion of the used biotesting devices therein. The biocidal interior surface and one-way valve in the receptacle form a sanitary method of containing contaminated biotesting devices. This combination allows the user to dispose of the receptacle, and safely and hygienically dispose of any contaminated biotesting devices and bodily fluid therein. The receptacle can be combined with a receptacle for unused biotesting devices, and/or sized to fit with or within a medical device, such as a test meter. In one form, the receptacle can be part of a care kit having a kit container for storing a lancing device, a testing device, and the disposal receptacle.

31 Claims, 5 Drawing Sheets

U.S. PATENT DOCUMENTS

| | | |
|---|---|---|
| 6,010,444 A | 1/2000 | Honeycutt et al. |
| 6,036,924 A | 3/2000 | Simons et al. |
| 6,116,780 A | 9/2000 | Young et al. |
| 6,749,063 B2 * | 6/2004 | Parker ................ 206/363 |
| 2002/0100706 A1 * | 8/2002 | Sherman et al. ........ 206/370 |
| 2003/0038047 A1 * | 2/2003 | Sleva et al. .......... 206/370 |
| 2003/0223906 A1 | 12/2003 | McAllister et al. |
| 2004/0173488 A1 | 9/2004 | Griffin et al. |

FOREIGN PATENT DOCUMENTS

| | | |
|---|---|---|
| EP | 0 885 591 A2 | 12/1998 |
| EP | 1 362 551 A1 | 11/2003 |
| EP | 1369083 A1 | 12/2003 |
| WO | WO92/20966 | 11/1992 |
| WO | WO99/12667 A1 | 3/1999 |
| WO | WO01/23885 A1 | 4/2001 |

* cited by examiner

BIOCIDAL BLOOD GLUCOSE STRIP AND LANCET OR SHARPS DISPOSAL DEVICE

BACKGROUND OF THE INVENTION

The present invention generally relates to a unique container for receiving and storing contaminated lancets and/or biosensors within the container and for having a biocidal interior surface. These devices are referred to as "biotesting devices". More specifically, but not exclusively, the present invention concerns a unique biocidal container that can be sized to fit within a medical device, such as a bioassay device, or the container can be part of a body fluid lancing and testing care kit. Moreover, a plurality of used biosensors and a plurality of unused biosensors can be stored in the same unique container.

Persons who analyze their bodily fluid, such as blood or interstitial fluid, for any number of characteristics, such as blood glucose levels for diabetics, must dispose of the used lancing devices, such as lancets, and used testing devices, such as biosensors. Disposal devices have been developed to store used lancets and/or used biosensors after the lancets or biosensors have been exposed to bodily fluid. The contaminated lancets and contaminated biosensors contained by a disposal device promote an environment in which bacteria can flourish. Typically, a liquid containing biocides is added to the disposal device to cover the lancets and biosensors therein. This liquid containing biocides produces biocidal activity within the disposal device to diminish and/or eliminate bacterial growth. One issue often associated with adding liquid containing biocides to a disposal device is that the user must pour the liquid into the disposal device without spilling the liquid outside the disposal device, while maintaining the contaminated lancets and biosensors within the disposal device. Another issue often associated with adding liquid containing biocides to a disposal device is that additional time and effort of the medical practitioner is required to add the liquid to the disposal device in order to safely dispose of the contaminated lancets and/or biosensors.

Patients who test their own blood glucose levels often encounter the situation in which they must safely dispose of their used lancet and used biosensor in a hygienic way. In a public setting, these patients often cannot find a disposal device in which used lancets and used biosensors will be disposed in a sanitary manner. Often these patients must carry their used lancets and/or biosensors with them until the patient can dispose of them in a sanitary manner. Typically, in a private setting, such as a home of a patient, a patient must expend time and energy to find the proper disposal device in their home in which the used lancets and used biosensors can be sanitarily disposed and contained within. Patients faced with these obstacles typically skip testing their blood glucose levels at the required time interval thereby risking an increased likelihood of an inappropriate blood glucose level, or they dispose of the devices in an inappropriate manner.

Another potential difficulty with a lancet disposal device and a biosensor disposal device is that often these devices are separate. For example, a lancet disposal device typically holds used lancets and a biosensor disposal device typically holds used biosensors. One problem associated with lancet disposal devices is the lancet disposal device typically is not configured to receive and contain used biosensors. Similarly, one problem associated with biosensor disposal devices is the biosensor disposal device typically is not configured to receive and contain used lancets. Moreover, these separate devices are additional to the lancing and testing devices already required by the user. These additional devices detract from the discretion that many diabetics prefer, and the person must spend time and energy searching for the separate devices.

Another obstacle often associated with a lancet and a biosensor is the safe disposal of the lancet and biosensor upon use of the lancet or biosensor. For example, the user or medical practitioner using the lancet would not want to accidentally prick another person or themselves with a contaminated lancet, thereby potentially exposing this person or themselves to disease. The user or medical practitioner using the biosensor would not want to accidentally touch another person or themselves with a contaminated biosensor, thereby potentially exposing this person or themselves to disease.

Thus, there remains the need for further improvement in this field.

SUMMARY

One aspect concerns a container for storing a medical instrument. The container includes a first compartment configured to store at least one of an unused biotesting device prior to lancing or testing a bodily fluid sample. The container also includes a second compartment connected with the first compartment, wherein the second compartment is configured to receive and contain at least one of a used biotesting device contaminated with the bodily fluid sample. Further, the second compartment includes a biocidal interior surface.

Another aspect concerns a device for storing a used biosensor. The device includes a container configured to hold the used biosensor contaminated with a bodily fluid sample and the container has a biocidal interior surface. The container also has a valve for receiving and containing the used biosensor within the container. The device also includes a test meter with a compartment sized to receive the container.

Yet another aspect includes a device for storing a contaminated medical device. The device includes a receptacle configured to hold at least one of a used lancet, a used biosensor, or a used integrated lancing test strip contaminated with a bodily fluid sample. The receptacle has an opening sized to receive and contain at least one of the used lancet, the used biosensor, or the used integrated lancing test strip within the receptacle. Additionally, the receptacle includes a biocidal interior surface.

Still yet another aspect includes a kit. At least one of a lancing device for containing a lancet, one or more containers for unused testing devices, and a test meter are stored in a kit container. Additionally, a receptacle is stored in the kit container. The receptacle has a biocidal interior surface and the receptacle is suitable for receiving a used biotesting device contaminated by a bodily fluid sample.

Further forms, objects, features, aspects, benefits, advantages, and embodiments of the present invention will become apparent from the detailed description and drawings provided herewith.

DESCRIPTION OF THE SELECTED EMBODIMENTS

Figure 1A:
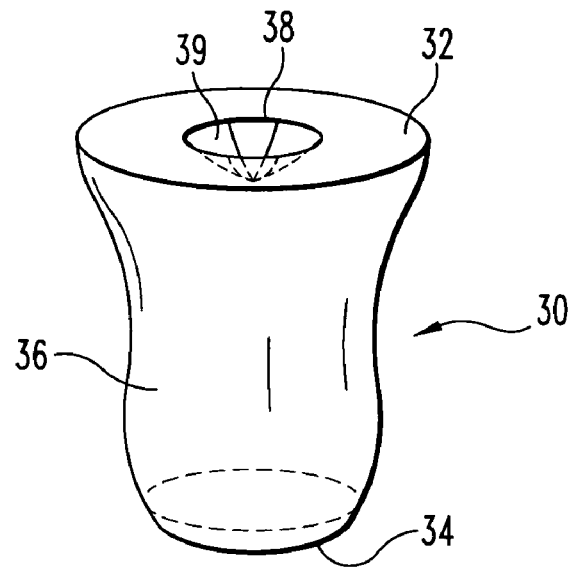
FIG. 1A is a perspective view of a receptacle for receiving used biotesting devices according to one embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The present invention generally concerns a biocidal receptacle for storing contaminated lancets, biosensors, and/or integrated lancing test strips. These and similar devices used for the sampling and testing of bodily fluids are collectively referred to herein as biotesting devices. Such biotesting devices have in common the fact that they are exposed to bodily fluids and therefore should be handled and disposed of in a manner that substantially eliminates the potential for contamination from the bodily fluid which they carry after use. The receptacle has a biocidal interior surface to diminish or eliminate bacterial growth from the contaminated lancets, biosensors, and/or integrated lancing test strips within the receptacle. The interior surface is rendered biocidal in any appropriate and acceptable manner, such as, for example, by coating the surface with a biocide, by impregnating the surface with a biocide, or by making the walls of the receptacle with biocide incorporated therein.

Additionally, the receptacle has a one-way opening or valve that allows contaminated lancets, test strips, integrated lancing test strips and associated bodily fluid, to be inserted into the receptacle. The one-way opening or valve prevents these contaminated lancets, test strips, integrated lancing test strips, and bodily fluid from escaping or being removed from the receptacle. As should be appreciated, the one-way opening in the receptacle safely contains used or contaminated biotesting devices and bodily fluid within the receptacle. Further, the risk of transferring a disease or cross-contamination from the contaminated lancets and biosensors is reduced with the biocidal interior surface and the one-way opening of the receptacle.

Optionally, the receptacle can be incorporated into or attached to another medical device to enable the user to carry the medical device and receptacle together. The incorporation of a receptacle or disposal device with a medical device enables the user to carry one device instead of multiple devices. Further, a user can discretely dispose of used lancets and test strips since the user no longer has to search for a separate disposal device, but instead can dispose of the used lancet and/or test strip at the time of lancing or testing. Additionally, the risk of cross-contamination from the used lancets and test strips contacting another person is reduced since the used lancets and test strips can be disposed in the receptacle at the time of use. Therefore, the user does not have to search for a separate disposal site while carrying a contaminated lancet and/or test strip. Beneficially, the one-way opening hermetically seals the used lancet and/or test strip within the receptacle to prevent odor from within the receptacle leaking out the one-way opening. Additionally, the one-way opening hermetically seals the receptacle thus the biocidal interior surface of the receptacle would not expire. Another benefit of the hermetic one-way opening is the biocidal interior surface will remain active for a longer time period as compared to a container in which a biocidal liquid is added to cover the contaminated biotesting devices.

Alternatively, a separate cover can attach over the one-way opening to cover the one-way opening after the user has deposited biotesting devices in the receptacle and the user is ready to dispose of the receptacle and contaminated biotesting devices therein. Optionally, the cover can be a plastic slip cover. Further, a notch can be positioned on the receptacle to align with the cover to hold the cover over the one-way opening and prevent the cover from being removed thereby exposing the one-way opening.

Selected features from different embodiments of the present invention will be described with reference to a bare lancet, a test strip, or an integrated lancing test strip, but it should nevertheless be appreciated that other types of lancing and/or testing devices can be used with the present invention. It is envisioned that multiple lancets, multiple test strips, and/or multiple integrated lancing test strips can be stored in a receptacle having a one-way opening and a biocidal effect within the receptacle. It is also envisioned that cassettes or drums containing multiple lancets, multiple test strips, or multiple integrated lancing test strips can be deposited in the biocidal receptacle through the one-way opening. Optionally, example lancing devices containing a lancet include Roche Diagnostics ACCU-CHEK® SAFE-T-PRO® lancing device and ACCU-CHEK® SOFTCLIX® lancing device. An example drum containing multiple lancets includes Roche Diagnostics ACCU-CHEK® MULTICLIX lancet drum. Representative test strips include Roche Diagnostics ACCU-CHEK® COMFORT CURVE® test strips and Roche Diagnostics ACCU-CHEK® AVIVA® blood glucose sensors. Representative test meters include Roche Diagnostics ACCU-CHEK® Advantage test meter and Roche Diagnostics ACCU-CHEK® AVIVA® blood glucose test meter.

A receptacle 30, according to one embodiment of the present invention, will now be described with reference to FIG. 1A. As shown in FIG. 1A, the receptacle 30 includes a top wall 32, a bottom wall 34, and a side wall 36 extending between the top wall 32 and the bottom wall 34. The top wall 32 defines a one-way opening or valve 38 configured to receive and retain lancets, test strips, and/or integrated lancing test strips.

In other embodiments, the opening 38 can be positioned in a wall other than the top wall 32. The top wall 32, bottom wall 34, and side wall 36 can be made of various materials, such as plastic or rubber to name a few. As shown, the receptacle 30 has a cylindrical shape; however, in other embodiments, the receptacle 30 may be shaped differently. For example, as shown in FIG. 1A, side wall 36 is continuous. In other embodiments, such as in a rectilinear configuration (not shown), the receptacle comprises more than one side wall 36.

An interior surface of the top wall 32 has a biocidal component. Similarly, an interior surface of the bottom wall 34 has a biocidal component and an interior surface of the side wall 36 also has a biocidal component. In one form, the interior surface of the receptacle 30 has a biocide material coated onto it. In another form, the receptacle 30 has a biocide impregnated into the interior surface. In yet another embodiment, the interior surface of the receptacle 30 is made of a biocidal material.

By way of non-limiting examples, suitable biocide materials include Saponified Phenols e.g., "STAPHENE®", commercially available from STERIS Corporation, Mentor, Ohio (surfactant properties), sodium dichloro-s-triazinctrione calcium hypochlorite, and perchloroethylene. Additionally, when the selected biocide material is a chlorinated biocide, agents such as cyanuric acid may be present on the interior surface with the biocide to protect the light sensitive compounds from rapid photo decay. It should be appreciated that other agents and pharmaceuticals affording biocidal benefits either broad spectrum or for targeted pathogens may be used. In one form, an admixture of biocidal material and a desiccant may be used to coat the interior surface of the receptacle 30. The admixture of biocidal material and desiccant may be printed or coated onto the interior surface of the receptacle 30. A non-limiting example of a printable biocide composition comprises a phosphate buffer, STAPHENE® biocide, polyethylene oxide, and $TiO_2$. To apply this biocide composition to the interior surface of the receptacle 30, aqueous or organic slurries commonly employed in the screen printing industry are pattern printed onto the interior surface of the receptacle 30 and dried to a prescribed level of water content before the receptacle 30 is used. Biocides are well known in the art and are commercially available from The Dow Chemical Company, Midland, Mich.; Great Lakes Chemical Corporation, West Lafayette, Ind.; and Bayer Corporation, Pittsburgh, Pa.

Printing or coating a biocidal material onto the interior surface of the receptacle 30 may be an easier method as compared to other methods of making the interior surface of the receptacle 30 biocidal. Other methods include impregnating the material of the interior surface with a biocide or making the interior surface with biocidal material. One example of impregnating the interior surface includes impregnating silica coated with a biocidal material into the interior surface made of plastic material.

Figure 1B:
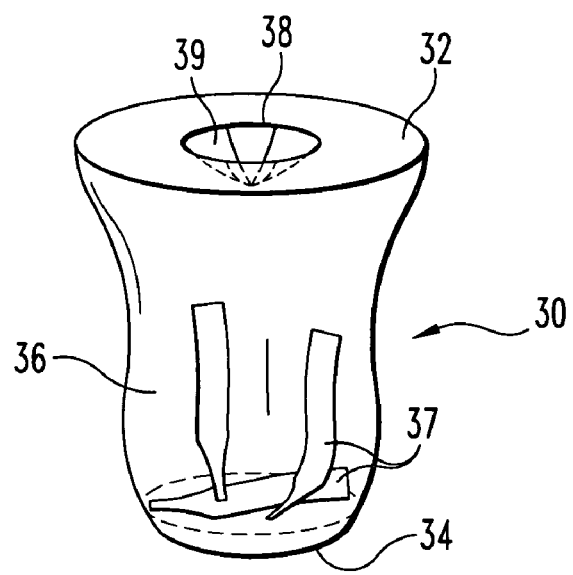
FIG. 1B is a perspective view of the receptacle containing used biotesting devices according to the embodiment shown in FIG. 1A.

As shown, the one-way opening 38 is circular in shape; however, in other embodiments the one-way opening 38 may be shaped differently. The one-way opening 38 includes a plurality of teeth 39 that are each substantially a triangular shape; however, in other embodiments the teeth 39 can be shaped differently. In a resting position, each of the teeth 39 is configured to touch another of the teeth 39 to form a hermetic seal over the one-way opening 38. This can be done by way of tight tolerances in positioning the teeth adjacently, or by substantial overlap, such as in an iris configuration. The teeth 39 are also flexible to bend towards the bottom wall 34. As lancets or other medical devices are inserted into the one-way opening 38, the teeth 39 flex or bend from the pressure of the lancets pressing against the teeth 39 to allow the lancets to pass through the one-way opening 38. After the lancets have passed over the teeth 39 and into the receptacle 30, the pressure is removed from the teeth 39 to allow the teeth 39 to relax back to the resting position, in which, the teeth 39 are in contact with one another to form the hermetic seal again. As should be appreciated, the teeth 39 are configured to bend towards the bottom wall 34 and relax back to the resting position; however, the teeth 39 are not configured to bend towards the top wall 32 to allow biotesting devices within the receptacle 30 to exit through the one-way opening 38. As shown in FIG. 1B, the receptacle 30 includes a plurality of biotesting devices 37.

It will be appreciated that alternatively the receptacle may include an opening that is configured in other manners to allow entry of the contaminated biotesting devices while at the same time preventing or substantially preventing escape of such devices. For example, it is known in the art to provide an entry pathway that is sufficiently torturous that as a practical matter a device can be inserted into the receptacle but it will not escape. In such an embodiment, it is contemplated that a separate cover may be attached over the opening when the receptacle is not in use. In one embodiment, the separate cover is configured to be removed when the receptacle is in use and replaced over the opening when the receptacle is not in use. In another embodiment, a user positions the cover over the opening after the user has finished with the receptacle and the separate cover is configured to remain attached over the opening.

The one-way opening 38 is sized to receive biotesting devices. Further, the one-way opening 38 allows lancing and/or testing devices to pass through it; however, the one-way opening 38 and teeth 39 also retain the lancing and/or testing devices within the receptacle 30. As mentioned previously, the combination of the biocidal interior surface and the one-way opening 38 reduces or eliminates bacterial growth within the receptacle 30 and safely stores the used lancets and/or test strips for disposal.

Further, the biocidal interior surface of the receptacle 30 eliminates the additional step of maintaining liquid containing biocides in the receptacle 30 to diminish bacterial growth from the contaminated medical devices within the receptacle 30. It is an aspect of the present invention that the receptacle is free from the presence of biocidal liquid. The user of the receptacle 30 no longer has to cover the contaminated medical devices within the receptacle 30 with liquid containing biocides to reduce bacterial growth; instead, the user must simply insert the contaminated medical devices through the one-way opening 38 and into the biocidal receptacle 30. The biocidal interior walls of the receptacle 30 generally reduce the bacterial growth from the contaminated medical devices without coating the medical devices with biocides. As should be appreciated, any corresponding odor from the contaminated lancets and/or test strips is reduced as the biocidal interior surface of receptacle 30 reduces the bacterial growth from contaminated lancets and/or test strips. Also, the risk of cross-contamination from used medical devices contacting another person is reduced since the used medical devices can be disposed and stored in the receptacle 30.

Figure 2:
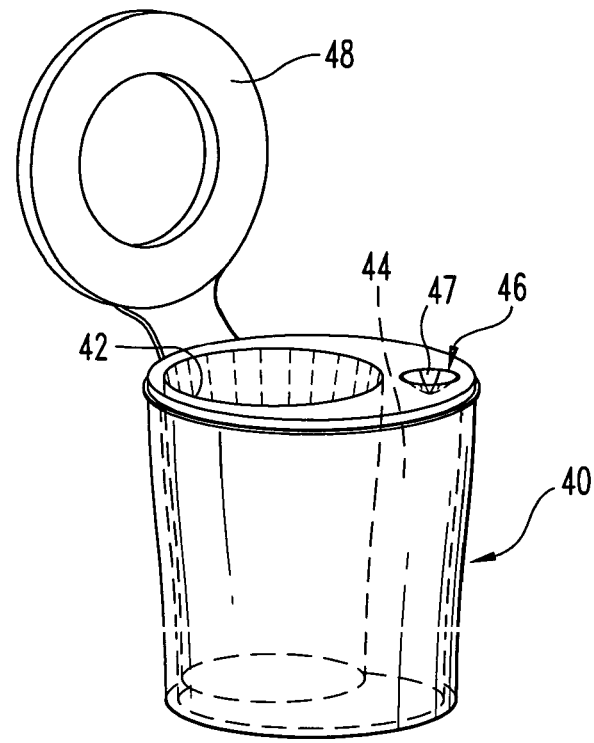
FIG. 2 is a perspective view of a container having a first compartment for unused biosensors and a second compartment for used biosensors according to another embodiment of the present invention.

A container 40, according to one embodiment of the present invention, will now be described with reference to FIG. 2. As shown in FIG. 2, container 40 includes a first compartment 42 for storing an unused lancet, an unused test strip, and/or an unused integrated lancing test strip prior to lancing or testing a bodily fluid sample. In one form, first compartment 42 is sized to store a plurality of unused lancets. In another form, the first compartment 42 can be sized to store a plurality of unused test strips and/or a plurality of unused integrated lancing test strips. Optionally, the first compartment 42 may contain a desiccant to keep moisture away from the unused test strips. Container 40 also includes a second compartment 44 connected to the first compartment 42. The second compartment 44 is configured to receive and contain a used lancet, a used test strip, and/or a used integrated lancing test strip contaminated with bodily fluid sample. The second compartment 44 includes a one-way opening or valve 46 similar to the one-way opening 38 as shown in FIG. 1A. Additionally, the second compartment 44 is similar to the receptacle 30 as shown in FIG. 1A. The second compartment 44, like receptacle 30, includes a biocidal interior surface. The one-way opening 46 includes a plurality of teeth 47, similar to the plurality of teeth 39. The one-way opening 46 is sized to receive and contain a used biotesting device. The combination of the biocidal interior surface and the one-way opening 46 reduces the possibility of cross-contamination or infection from contaminated lancets and/or test strips contacting another person after the lancets and/or test strips are disposed. In one form, either or both of the first compartment 42 and the second compartment 44 are sized to store at least ten (10) used biotesting devices, optionally at least fifty (50) or at least one-hundred (100) used biotesting devices. The first compartment 42 and the second compartment 44 can be made of various materials, such as plastic, metal, or rubber to name a few.

As shown in FIG. 2, the container 40 includes a lid 48. In this embodiment, lid 48 is connected with container 40 to form a flip-top lid that seals the first compartment 42 and the second compartment 44. In other embodiments, the container 40 may have a different enclosure other than lid 48, for example, a lid that screws onto the container 40 or a lid that slides to expose the first compartment 42 and/or the second compartment 44. The container may also include separate covers for each of the compartments.

As illustrated, the container 40 enables a user to simultaneously carry unused lancets and/or test strips and sanitarily dispose of these lancets and/or test strips after using them. As should be appreciated, the combination of the first compartment 42 storing unused biotesting devices and the second compartment 44 storing used biotesting devices enables the user to carry one device with them instead of multiple devices. Beneficially, a user can discretely dispose of used biotesting devices since the user no longer has to search for a separate disposal device, but instead can dispose of the used biotesting devices at the time of lancing or testing. The biocidal interior surface of the second compartment 44 reduces bacterial growth from the contaminated lancets and/or test strips and reduces odor associated with bacterial growth. Additionally, the risk of cross-contamination from the used lancets and test strips contacting another person is reduced since the used lancets and test strips can be disposed in the second compartment 44 at the time of testing.

Figure 3:
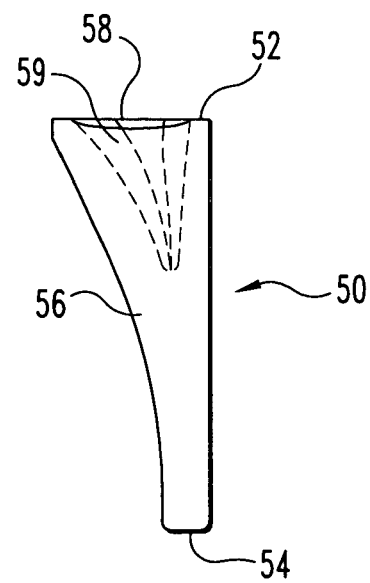
FIG. 3 is a front view of a container for receiving used biotesting devices according to yet another embodiment of the present invention.

In another embodiment, as shown in FIG. 3, a container 50 similar to receptacle 30 is shown. Container 50 includes a top wall 52, a bottom wall 54, and a side wall 56 extending between the top wall 52 and the bottom wall 54. As shown, the container 50 has a triangular or horn-shape; however, the container 50 can be shaped differently. The container 50 includes a one-way opening 58 in the top wall 52. In other embodiments, the one-way opening 58 can be located in another of the walls 54 or 56. The one-way opening 58 includes a plurality of teeth 59 similar to the teeth 47 of receptacle 40. The one-way opening 58 is configured to receive and retain lancets, test strips, and/or integrated lancing test strips. In this form, the top wall 52, the bottom wall 54, and the side wall 56 are made of a semi-pliable plastic. In another form, the top wall 52, the bottom wall 54, and the side wall 56 are made of a high density flexible plastic. Yet in other embodiments, the top wall 52, the bottom wall 54, and the side wall 56 are made of rubber. An interior surface of the top wall 52, an interior surface of the bottom wall 54, and an interior surface of the side wall 56 are impregnated or coated with a biocidal substance. Optionally, the walls 52, 54, and 56 are made of a biocidal material, for example a semi-pliable biocidal plastic material.

Figure 4:
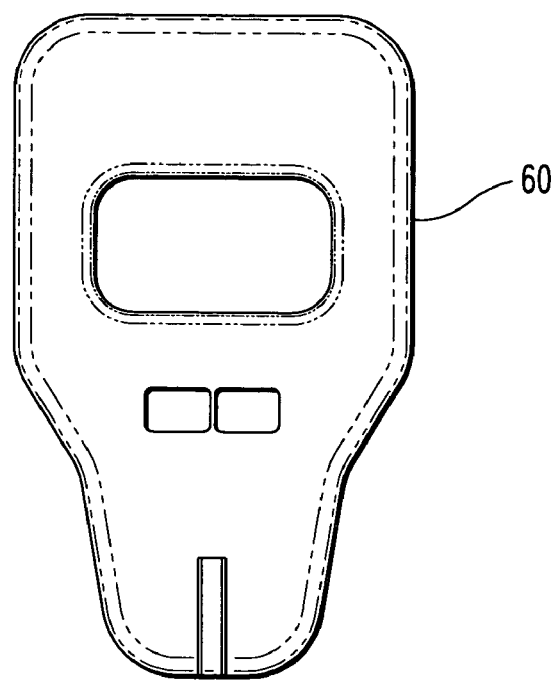
FIG. 4 is a front view of a bioassay device for storing the container according to the embodiment shown in FIG. 3.
Figure 5A:
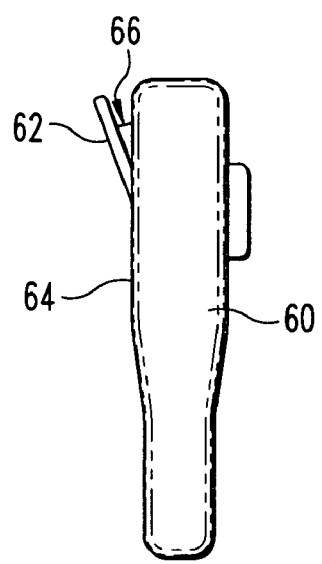
FIG. 5A is a front view of the bioassay device according to the embodiment shown in FIG. 4.

The container 50 is sized to fit within a test meter 60 (shown in FIG. 4). The test meter 60 is a testing device used, for example, to determine the blood glucose levels in a bodily fluid sample from a person, usually a diabetic. The test meter 60 includes a drawer 62 as shown in FIG. 5A. In this form, the drawer 62 ejects or rotates open from a side 64 of the test meter 60. In other forms, the test meter 60 can include another form of closure for the used strip compartment 66 other than the drawer 62. As should be appreciated, the container 50 may be made of a semi-pliable plastic, thereby allowing it more easily to conform to or fit into a used lancet or test strip compartment 66 of the test meter 60. The test strip compartment 66 rotates open to form a triangular shape. As shown, the container 50 having a similar triangular shape and size as the test strip compartment 66 maximizes the potential storage space for used test strips within the test strip compartment 66.

In use, the container 50 is inserted into the used test strip compartment 66 of the test meter 60. Next, the drawer 62 is opened to expose the container 50 and the used test strip compartment 66. A user then inserts a contaminated lancet or test strip through the one-way opening 58 and into the container 50. The biocidal interior surface of the container 50 eliminates or reduces bacteria and disease from the contaminated lancets and/or test strips while the one-way opening 58 and the plurality of teeth 59 safely retain the used lancets and/or test strips within the container 50. The drawer 62 is then closed. Beneficially, the user can carry the test meter 60 and disposal container 50 for discretely storing used lancets and/or test strips. Storing the container 50 in the used test strip compartment 66 of the test meter 60 enables the user to dispose of used test strips at the time of use. At any time, the user can remove the container 50 containing used test strips and insert an empty container into the test meter 60. Removing the container 50 from the test meter 60 promotes a hygienic disposal of the container 50 and the contaminated test strips within the container 50. The combination of the biocidal interior surfaces and the one-way opening 58 reduces the possibility of cross-contamination or infection from contaminated lancets and/or test strips contacting another person after the lancets and/or test strips are disposed. Additionally, the container 50 allows a user to safely dispose of contaminated test strips. In this form, the empty test meter 60 is ready for insertion of another container.

Figure 5B:
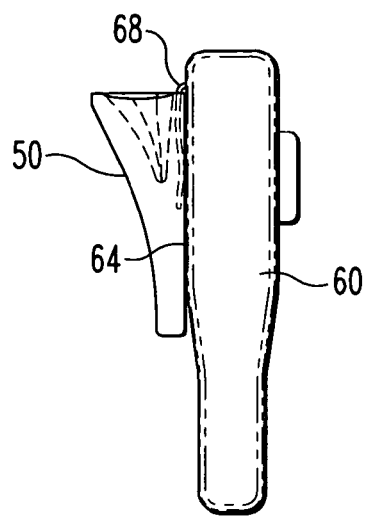
FIG. 5B is a front view of another bioassay device for storing the container according to the embodiment shown in FIG. 3.

Optionally, an exterior surface of the test meter 60 may contain a fastener or clip 68 to attach the container 50 to the test meter 60 as shown in FIG. 5B. The clip 68 is attached to the exterior surface of the test meter 60 to hold the container 50 until the user is ready to detach the container 50 from the clip 68 and dispose of the container 50 and any contaminated biotesting devices therein. As should be appreciated, the exterior surface of the test meter 60 and the container 50 may be configured in various manners to detachably attach the container 50 to the test meter 60.

In one form, the test meter 60 includes a lancet container configured to store a plurality of unused lancets. As should be appreciated, the plurality of unused lancets becomes a plurality of used lancets after each lancet forms an incision in a user's skin. The container 50 is sized to store the plurality of used lancets. In another form, the test meter 60 includes a test strip container configured to store a plurality of unused test strips. As should be appreciated, the plurality of unused test strips becomes a plurality of used test strips after testing a bodily fluid sample. The container 50 is sized to store the plurality of used test strips. Beneficially, the user can carry a plurality of unused test strips and a plurality of used test strips in the test meter 60 which gives the user the ability to test a bodily fluid sample and sanitarily and safely dispose of the used test strip in a public or private setting. In yet another form, the test meter 60 includes an integrated lancing test strip container configured to store a plurality of unused integrated lancing test strips. In this form, the plurality of unused integrated lancing test strips becomes a plurality of used integrated lancing test strips upon lancing a user and testing a bodily fluid sample. The container 50 is sized to store the plurality of used integrated lancing test strips. As mentioned previously, the user can carry a plurality of unused integrated lancing test strips and a plurality of used integrated lancet test strips in the test meter 60 which gives the user the ability to form an incision, test the bodily fluid sample from the incision, and sanitarily dispose of the used integrated lancing test strip in the container 50. As should be appreciated, the combination of container 50 and integrated lancing test strips in the test meter 60 encourages a diabetic to regularly test his or her blood glucose levels since the combination forms an all-in-one lancing, testing, and disposal device. When the test meter uses separate testing devices, such as separate lancing devices and test strips, then the meter may include one large container or multiple containers sized to contain the used testing devices.

Figure 6:
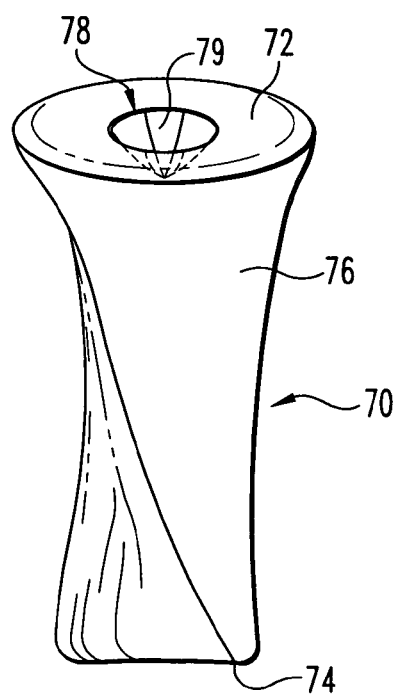
FIG. 6 is a perspective view of a receptacle for receiving used biotesting devices according to another embodiment of the present invention.

A flexible or expandable receptacle 70, according to another embodiment of the present invention, will now be described with reference to FIG. 6. Expandable receptacle 70 is similar to the receptacle 30. As shown in FIG. 6, the receptacle 70 includes a top wall 72, a bottom wall 74, and a continuous side wall 76 extending between the top wall 72 and the bottom wall 74. The top wall 72 defines a one-way opening or valve 78 similar to the one-way opening 38. In other embodiments, the one-way opening 78 can be located in another of the walls 74 or 76. The one-way opening 78 includes a plurality of teeth 79 similar to the teeth 39 of receptacle 30. The receptacle 70 is triangularly shaped; however, the receptacle 70 may be other shapes, such as rectangular, circular, or trapezoidal to name a few. In one embodiment, the side wall 76 is made of a material that allows for expansion, thereby creating a larger cavity within the receptacle 70 for used lancets and/or test strips. For example, side wall 76 can be made of a pleated plastic material. As another example, side wall 76 can be made of a material that is pleated to allow for expansion from lancets and/or test strips placed in the receptacle 70.

The receptacle 70 has a biocidal interior surface to kill bacteria or disease from the contaminated lancets and/or test strips placed therein. In one embodiment, the receptacle 70 includes a biocide coated onto the interior surface of the receptacle 70. In another embodiment, the receptacle 70 includes a biocide impregnated into the interior surface of the receptacle. In a third embodiment, the interior surface of the receptacle 70 is made of a biocidal material.

Optionally, the one-way opening 78 is sized to receive a drum or other type of cartridge containing a plurality of used biosensors or a drum containing a plurality of used lancets. The one-way opening 78 prevents used lancets, used test strips, and/or fluid from escaping or being removed from the receptacle 70; however, the one-way 78 opening allows for insertion of a test strip and/or a lancet into the receptacle 70.

The biocidal interior surface and one-way opening 78 of the receptacle 70 reduce the risk that a disease from a contaminated lancet or test strip will be passed to another person from contact as the biocidal interior surface kills the bacteria within the receptacle 70 and the one way opening 78 retains the contaminated lancets or test strips within the receptacle 70.

Figure 7:
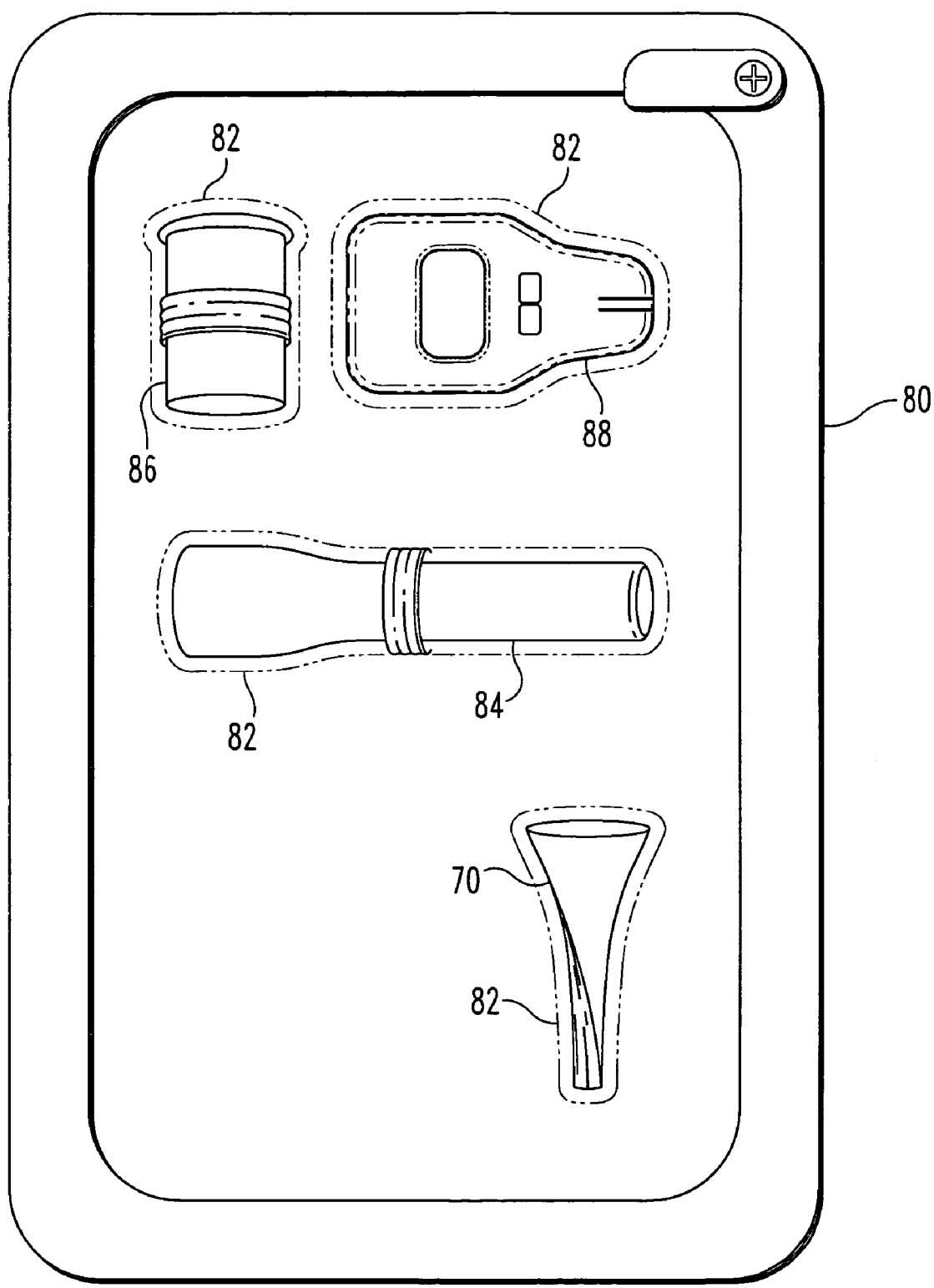
FIG. 7 is a front view of a kit container storing a lancing device, a bodily fluid testing meter, a test strip container, and the receptacle device according to the embodiment shown in FIG. 6.

As shown in FIG. 7, the receptacle 70 may be stored in a kit container 80. The kit container 80 is rectangular in shape; however, in other embodiments the kit container 80 may be shaped differently. The kit container 80 includes a plurality of compartments 82 sized to receive various medical devices. A lancing device 84 having at least one lancet is stored in one of the compartments 82 of the kit container 80. Optionally, the lancing device 84 includes a plurality of lancets. A test strip container 86 having at least one test strip is stored in another of the compartments 82 of the kit container 80. Optionally, the test strip container 86 includes a plurality of test strips. As shown in FIG. 7, a test meter 88 is stored in yet another of the compartments 82 of the kit container 80. As should be appreciated, in other forms, the kit container 80 may store other embodiments of the lancing device, test strip container, and test meter. Although not shown, the kit container 80 may also store a plurality of lancets, a plurality of test strips, or a plurality of integrated lancet test strips in a cassette or drum. The ability of a user to transport and store all of their bodily fluid lancing and testing equipment and the receptacle 70 in a single kit container 80 to form an all-in-one product for the user increases the portability of multiple devices. Alternatively, the receptacle may be included in the kit in one of the other disclosed embodiments—e.g., attached to a biotesting device container or combined with the test meter.

As mentioned previously, in one form, the receptacle 70 is configured to expand after a predetermined number of lancets are placed within the receptacle 70. As should be appreciated, the receptacle 70 is sized to receive a predetermined number of lancets; however, additional lancets can be placed within the receptacle 70 to expand the volume capacity of the receptacle 70. The ease of disposal of lancets or test strips through the one-way opening 78 into the receptacle 70 encourages users to lance and test their bodily fluid samples at regularly scheduled times since the users have a safe and sanitary method of disposal of the lancets and test strips in the receptacle 70. Additionally, users are able to discretely dispose of their used lancets and test strips into receptacle 70 without having to search for a separate disposal site not previously contained in their kit container 80.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device for storing a contaminated medical device, comprising:
   a receptacle configured to hold at least one biotesting device contaminated with a bodily fluid sample, the receptacle defining an opening sized to receive and contain at least one said contaminated biotesting device within the receptacle, the opening includes a plurality of teeth configured to form a hermetic seal; and
   wherein said receptacle includes a biocidal interior surface.

2. The device of claim 1, wherein:
   the biocidal interior surface of the receptacle includes a biocide coated onto the interior surface of the receptacle.

3. The device of claim 1, wherein:
   the biocidal interior surface of the receptacle includes a biocide impregnated into the interior surface of the receptacle.

4. The device of claim 1, wherein:
the biocidal interior surface of the receptacle is made of a biocidal material.

5. The device of claim 1, wherein:
the receptacle is sized to hold a plurality of contaminated biotesting devices.

6. The device of claim 1, wherein:
the contaminated biotesting devices comprise a volume; and
the receptacle is sized to hold a predetermined volume of the contaminated biotesting devices, and further wherein the receptacle is configured to expand to hold an additional volume of the contaminated biotesting devices.

7. The device of claim 6, wherein:
the receptacle is made of a semi-pliable plastic.

8. The device of claim 6, wherein:
the receptacle includes pleated walls for expansion to hold the additional volume of the contaminated biotesting devices.

9. The device of claim 1, wherein:
the plurality of teeth is configured to bend as the contaminated biotesting devices are inserted into the opening.

10. The device of claim 9, wherein:
the receptacle contains a top wall, a bottom wall, and a side wall configured to connect the top wall and the bottom wall, the top wall defines the opening; and
the plurality of teeth is configured to bend toward the bottom wall.

11. A container for storing a medical instrument, comprising:
a first compartment configured to store at least one unused biotesting device; and
a second compartment connected with the first compartment, wherein the second compartment defines a one-way opening configured to receive and contain within the compartment at least one biotesting device contaminated with a bodily fluid sample, the one-way opening includes a plurality of teeth configured to form a hermetic seal over the opening, the second compartment including a biocidal interior surface.

12. The container of claim 11, wherein:
the second compartment is sized to receive and contain at least 10 said contaminated biotesting devices.

13. The container of claim 11, wherein:
the second compartment is sized to receive and contain at least =said contaminated biotesting devices.

14. The container of claim 11, wherein:
the second compartment is sized to receive and contain at least 100 said contaminated biotesting devices.

15. The container of claim 11, wherein:
the plurality of teeth is configured to bend as the contaminated biotesting devices are inserted into the one-way opening.

16. The container of claim 11, wherein:
the biocidal interior surface of the second compartment includes a biocide coated onto the interior surface of the second compartment.

17. The container of claim 11, wherein:
the biocidal interior surface of the second compartment includes a biocide impregnated into the interior surface of the second compartment.

18. The container of claim 11, wherein:
the biocidal interior surface of the second compartment is made of a biocidal material.

19. A test meter device including means for storing a used biotesting device, comprising:
a container configured to hold said used biotesting device contaminated with a bodily fluid sample, the container having a biocidal interior surface, the container further defining a one-way opening for receiving and containing the used biotesting device within the container, the one-way opening includes a plurality of teeth configured to form a hermetic seal over the opening, each of the plurality of teeth being in contact with another of the plurality of teeth; and
a test meter having a compartment receiving the container therein.

20. The device of claim 19, wherein:
the test meter comprises a lancet container configured to store a plurality of unused lancets.

21. The device of claim 19, wherein:
the test meter comprises a test strip container configured to store a plurality of unused test strips.

22. The device of claim 19, wherein:
the biocidal interior surface of the container includes a biocide coated onto the interior surface of the container.

23. The device of claim 19, wherein:
the biocidal interior surface of the container includes a biocide impregnated into the interior surface of the container.

24. The device of claim 19, wherein:
the biocidal interior surface of the container is made of a biocidal material.

25. The device of claim 19, wherein:
the container is made of a semi-pliable plastic.

26. A test meter device including means for storing a used biotesting device, comprising:
a container configured to hold said used biotesting device contaminated with a bodily fluid sample, the container having a biocidal interior surface, the container further defining a one-way opening for receiving and containing the used biotesting device within the container, the container being sized to hold a predetermined volume of said used biotesting devices, and wherein the container is configured to expand to hold an additional volume of said used biotesting devices; and
a test meter having means for attaching the container to the test meter.

27. The device of claim 26, wherein:
the means for attaching the container to the test meter includes a clip.

28. A kit, comprising:
a kit container;
at least one container for containing an unused biotesting device and a test meter, stored in the kit container; and
a receptacle stored in the kit container, the receptacle having a biocidal interior surface and the receptacle suitable for receiving at least one used biotesting device contaminated by a bodily fluid sample, the receptacle further defining a one-way opening for receiving and containing the used biotesting device within the receptacle, the one-way opening includes a plurality of teeth, each of the plurality of teeth positioned to touch another of the plurality of teeth to form a hermetic seal over the opening.

29. The kit of claim 28, wherein:
the biocidal interior surface of the receptacle includes a biocide coated onto the interior surface of the receptacle.

30. The kit of claim 28, wherein:
the biocidal interior surface of the receptacle includes a biocide impregnated into the interior surface of the receptacle.

31. The kit of claim 28, wherein:
the biocidal interior surface of the receptacle is made of a biocidal material.

* * * * *

UNITED STATES PATENT AND TRADEMARK OFFICE
CERTIFICATE OF CORRECTION

| | | |
|---|---|---|
| PATENT NO. | : 7,516,847 B2 | Page 1 of 1 |
| APPLICATION NO. | : 11/151971 | |
| DATED | : April 14, 2009 | |
| INVENTOR(S) | : Sienna Lea Henning | |

It is certified that error appears in the above-identified patent and that said Letters Patent is hereby corrected as shown below:

Col. 11 in claim 13, line 3, please remove the set of double lines that appears before the word "said" and insert therefor the number --50--.

Signed and Sealed this

Twenty-sixth Day of May, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,516,847 B2 | Page 1 of 1 |
| APPLICATION NO. | : 11/151971 | |
| DATED | : April 14, 2009 | |
| INVENTOR(S) | : Sienna Lea Henning | |

It is certified that error appears in the above-identified patent and that said Letters Patent is hereby corrected as shown below:

Col. 11 in claim 13, line 45, please remove the set of double lines that appears before the word "said" and insert therefor the number --50--.

This certificate supersedes the Certificate of Correction issued May 26, 2009.

Signed and Sealed this

Sixteenth Day of June, 2009

JOHN DOLL
*Acting Director of the United States Patent and Trademark Office*